United States Patent [19]

Atkinson et al.

[11] Patent Number: 5,441,484
[45] Date of Patent: Aug. 15, 1995

[54] BALLOON DILATATION CATHETER HAVING A FREE CORE WIRE

[75] Inventors: Robert Atkinson, St. Anthony; Carol Loney, St. Louis Park, both of Minn.

[73] Assignee: SciMed Life Systems, Inc., Maple Grove, Minn.

[21] Appl. No.: 162,835

[22] Filed: Dec. 6, 1993

Related U.S. Application Data

[63] Continuation of Ser. No. 852,545, Mar. 17, 1992, abandoned.

[51] Int. Cl.⁶ .......................................... A61M 29/00
[52] U.S. Cl. ...................................... 604/96; 606/194
[58] Field of Search ................................. 604/95–103; 606/192, 194; 128/656–658

[56] References Cited

U.S. PATENT DOCUMENTS

| | | |
|---|---|---|
| 3,402,717 | 9/1968 | Doherty . |
| 3,837,347 | 9/1974 | Tower . |
| 4,261,339 | 4/1981 | Hanson et al. . |
| 4,413,989 | 11/1983 | Schjeldahl et al. . |
| 4,606,347 | 8/1986 | Fogarty et al. . |
| 4,616,653 | 10/1986 | Samson et al. ................. 128/657 X |
| 4,715,378 | 12/1987 | Pope, Jr. et al. . |
| 4,771,778 | 9/1988 | Mar . |
| 4,793,350 | 12/1988 | Mar et al. . |
| 4,813,934 | 3/1989 | Engelson et al. . |
| 4,821,722 | 4/1989 | Miller et al. . |
| 4,838,268 | 6/1989 | Keith et al. . |
| 4,846,174 | 7/1989 | Willard et al. ................. 606/194 |
| 4,848,344 | 7/1989 | Sos et al. . |
| 4,917,088 | 4/1990 | Crittenden . |
| 4,943,278 | 7/1990 | Euteneuer et al. . |
| 4,964,409 | 10/1990 | Tremulis ................. 128/657 |
| 4,976,720 | 12/1990 | Machold et al. . |
| 4,998,917 | 3/1991 | Gaiser et al. . |
| 4,998,923 | 3/1991 | Samson et al. . |
| 5,002,559 | 3/1991 | Tower . |
| 5,003,989 | 4/1991 | Taylor et al. ................. 128/772 |
| 5,032,113 | 7/1991 | Burns . |
| 5,042,985 | 8/1991 | Elliott et al. . |
| 5,055,109 | 10/1991 | Gould et al. . |
| 5,059,176 | 10/1991 | Winters . |
| 5,102,390 | 4/1992 | Crittenden et al. . |
| 5,104,376 | 4/1992 | Crittenden . |
| 5,135,487 | 8/1992 | Morrill et al. ................. 604/96 |
| 5,135,494 | 8/1992 | Engelson et al. . |
| 5,141,518 | 8/1992 | Hess et al. ................. 606/194 |
| 5,156,595 | 10/1992 | Adams . |
| 5,171,221 | 12/1992 | Samson . |
| 5,195,989 | 3/1993 | Euteneuer . |
| 5,209,728 | 5/1993 | Kraus et al. . |
| 5,246,420 | 9/1993 | Kraus et al. . |
| 5,256,144 | 10/1993 | Kraus et al. ................. 604/96 |
| 5,318,529 | 6/1994 | Kontos ................. 604/96 |
| 5,324,259 | 6/1994 | Taylor et al. ................. 604/96 |
| 5,324,263 | 6/1994 | Kraus et al. ................. 604/96 |

FOREIGN PATENT DOCUMENTS

| | | |
|---|---|---|
| 0368523A2 | 10/1989 | European Pat. Off. . |
| 0462801A1 | 6/1991 | European Pat. Off. . |
| 0528294A2 | 8/1992 | European Pat. Off. . |
| WO91/13649 | 9/1991 | WIPO . |

Primary Examiner—Corrine Maglione
Attorney, Agent, or Firm—Nawrocki, Rooney & Sivertson

[57] ABSTRACT

A non-over-the-wire catheter for use in angioplasty including a core wire which extends distally beyond a distal end of a tubular member. The tubular member defines an interior passage which is in fluid communication with a distal interior passage of a waist tube that extends about the core wire. An inflatable balloon member extends about the core wire and is in fluid communication with the distal interior passage of the waist tube. An axially stiff component is coupled to the balloon member. The axially stiff component permits rotational movement of the core wire relative to the balloon member so that torque applied to the tubular member and conveyed to the core wire is not readily transmitted to the balloon member. A push element associated with the core wire abuts the axially stiff component. The push element prevents longitudinal displacement of the inner sleeve relative to the core wire, which in turn prevents a longitudinal collapse of the balloon member and waist tube when the catheter is advanced through a patient's vascular system.

22 Claims, 6 Drawing Sheets

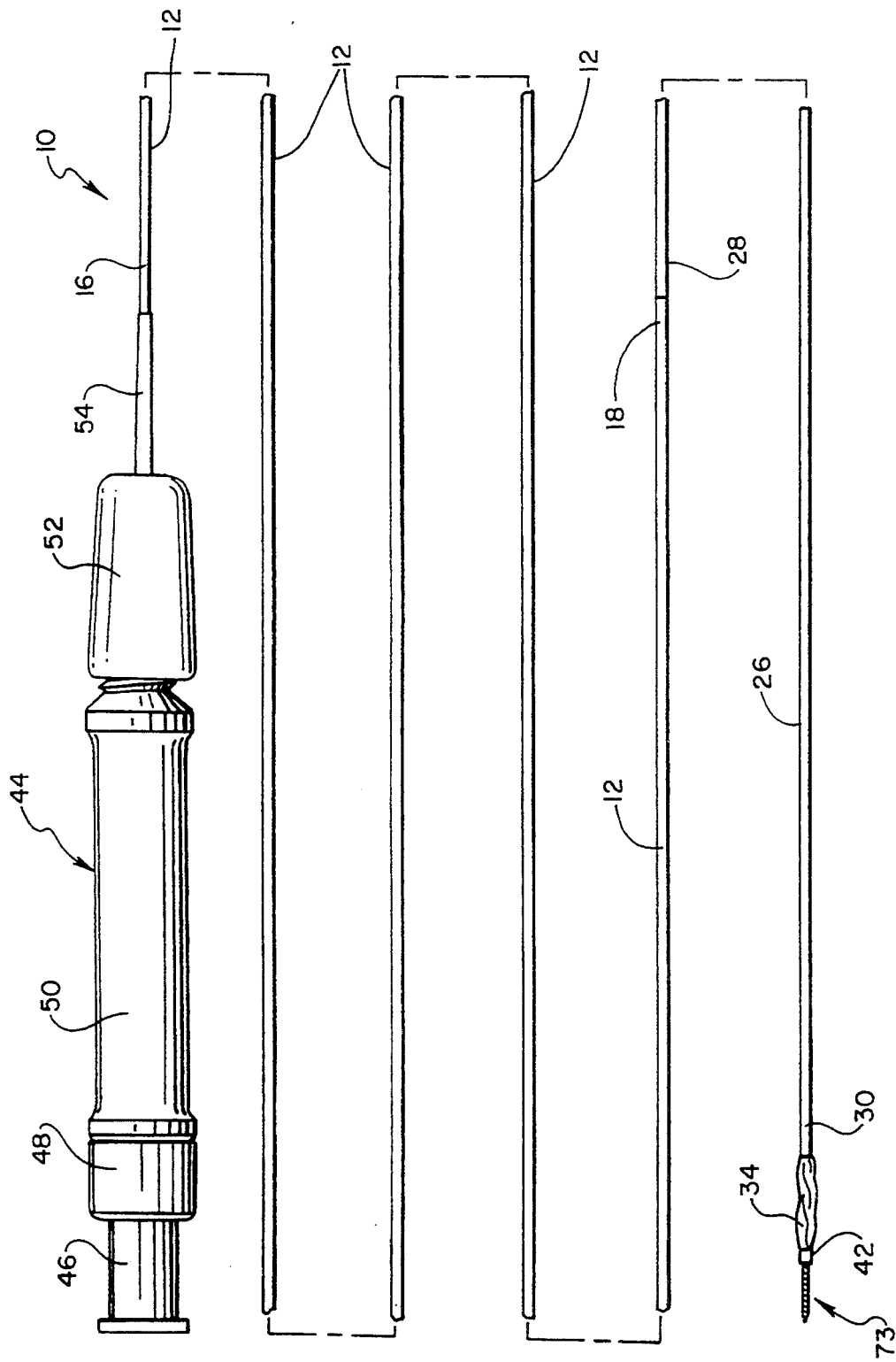

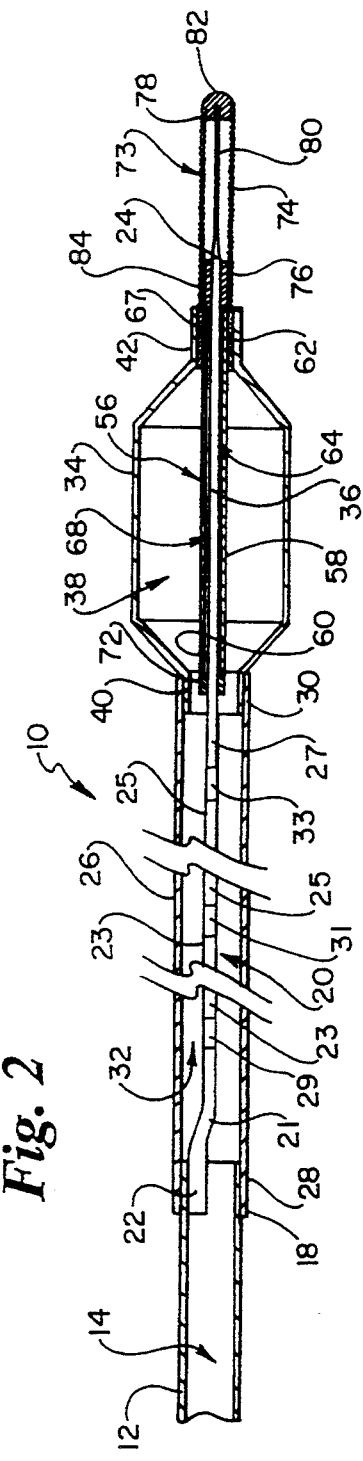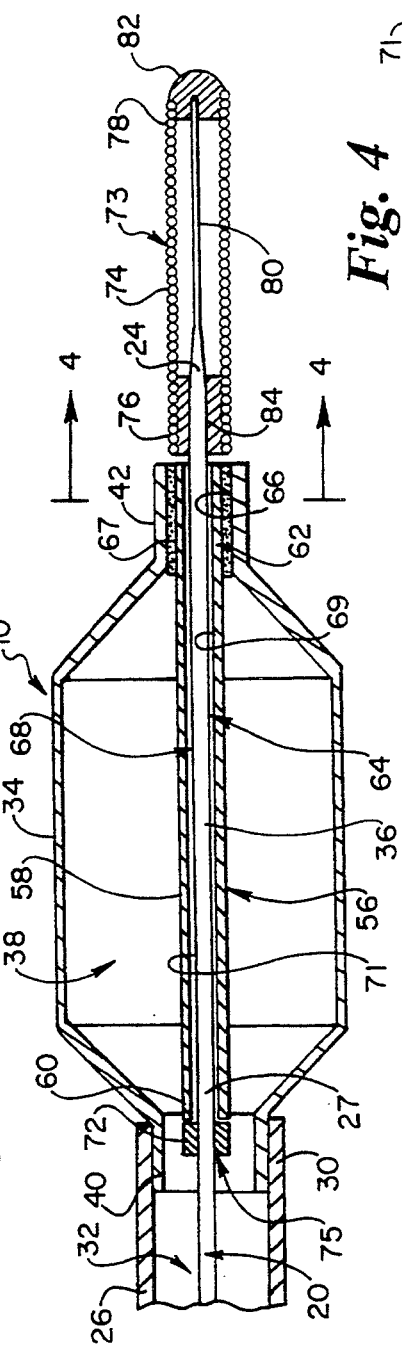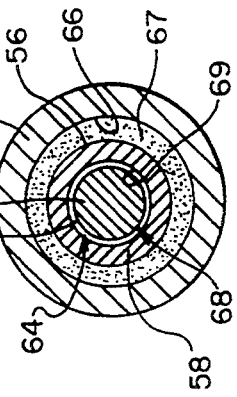

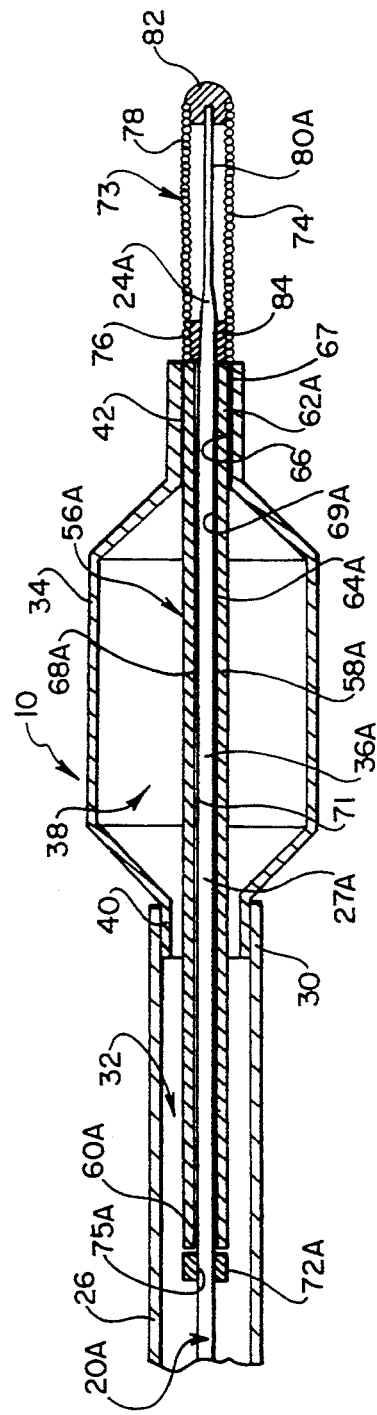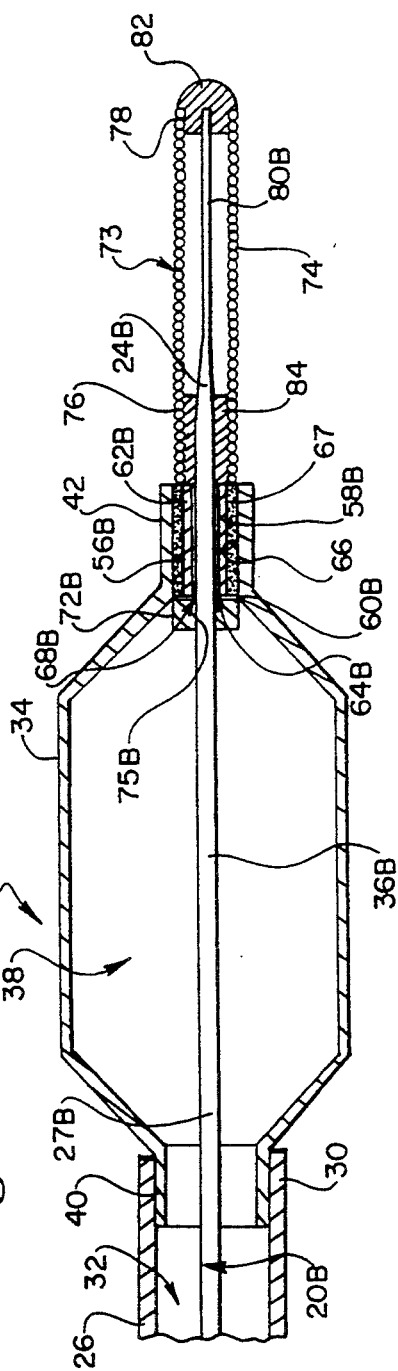

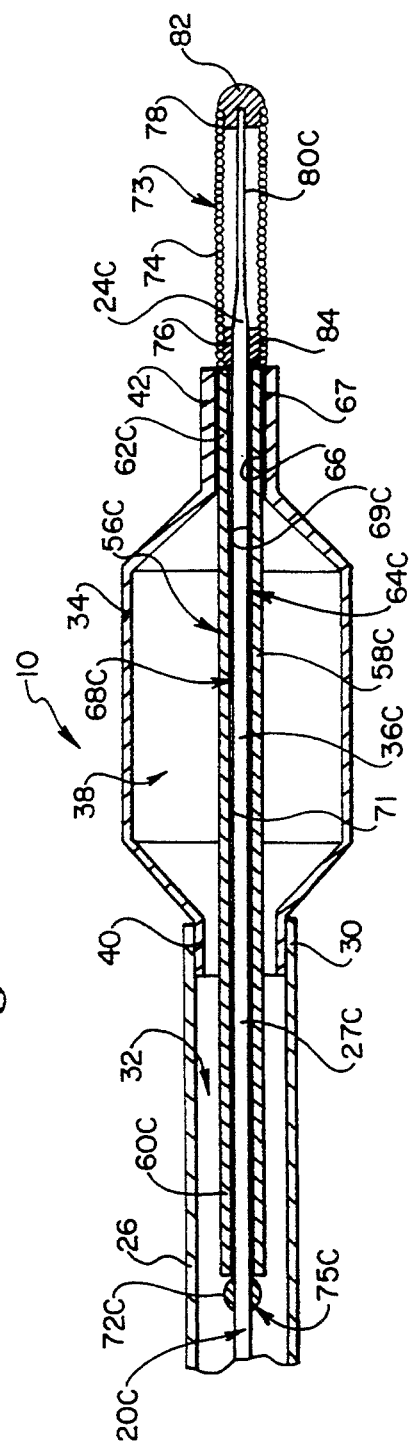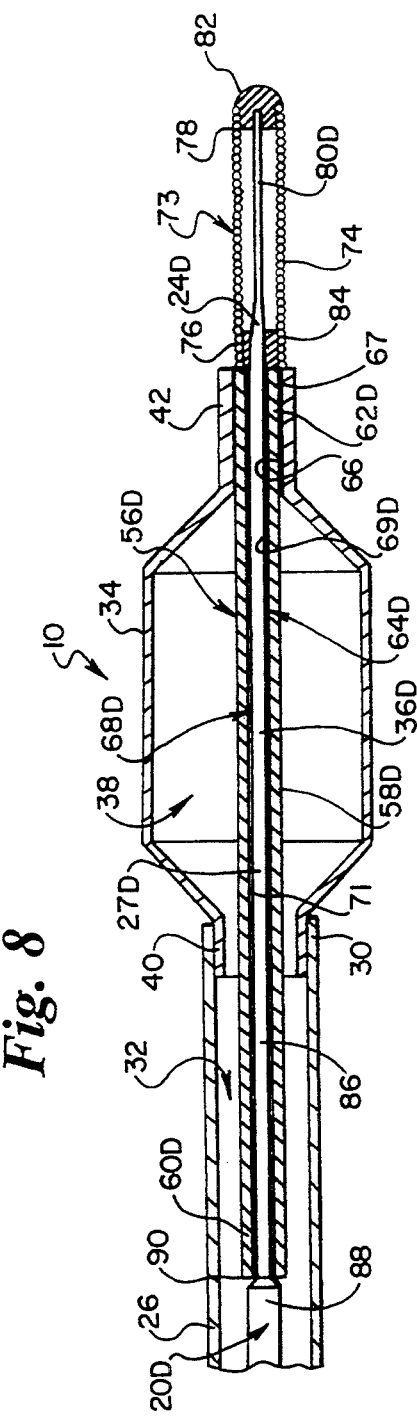

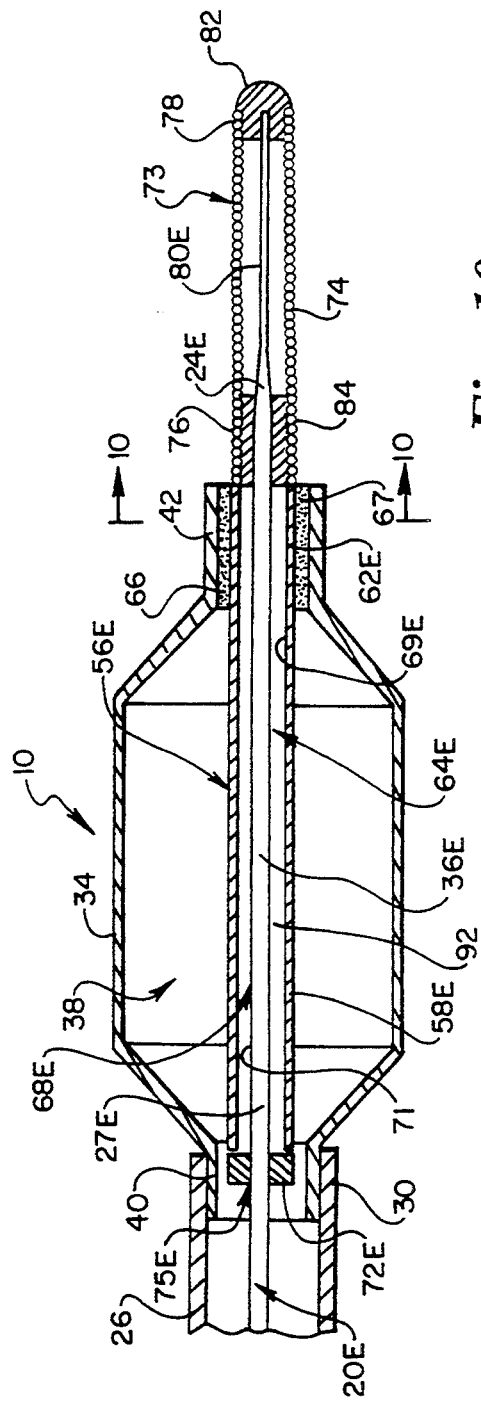
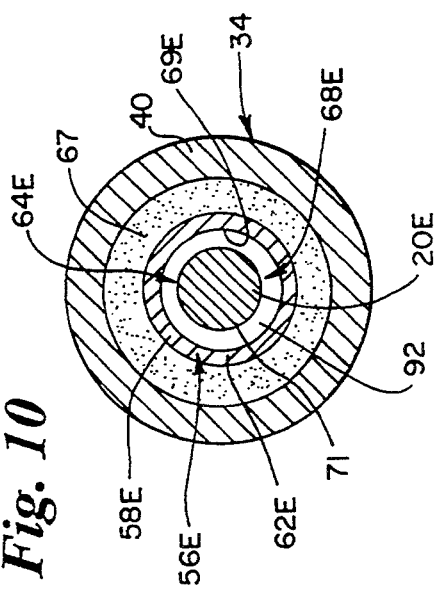
Fig. 9
Fig. 10

BALLOON DILATATION CATHETER HAVING A FREE CORE WIRE

This is a continuation of application Ser. No. 07/852,545 filed on Mar. 17, 1992, now abandoned.

REFERENCE TO COPENDING APPLICATIONS

Reference is made to the following commonly assigned applications which were filed on even date with this application and are entitled as follows:

(1) Balloon Dilatation Catheter Having A Torsionally Soft Component (Ser. No. 07/852,547); and (2) Balloon Dilatation Catheter Having Dual Sealing Plugs (Ser. No. 07/852,546).

BACKGROUND OF THE INVENTION

The present invention relates to the field of percutaneous transluminal coronary angioplasty (PTCA). In particular, the present invention is a non-over-the-wire dilatation balloon catheter.

Angioplasty has gained wide acceptance in recent years as an efficient and effective method for treating certain types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Typically, the catheter is introduced and directed partially through a patient's vascular system via a guide catheter. Using fluoroscopy, a physician guides the catheter through that portion of the patient's vascular system distal of the guide catheter until the balloon is positioned across the stenosis. While the catheter is being steered through the vascular system, the balloon is in a deflated state, wrapped (i.e., folded) tightly about the distal end of the catheter to reduce the profile of the balloon. Reducing the profile of the balloon allows the catheter to easily travel through the guide lumen of the guide catheter and traverse arterial vessels and stenoses having small through openings. Once the catheter is positioned with the balloon across the stenosis, the balloon is inflated by supplying fluid under pressure through an inflation lumen to the balloon. Inflation of the balloon causes stretching of the artery and pressing of the lesion into the artery wall to re-establish an acceptable blood flow through the artery.

Over-the-wire catheters and non-over-the-wire catheters are two types of dilatation catheters that are commonly used in angioplasty. An over-the-wire catheter has an inflation lumen and a guide wire lumen through which a separate guide wire is advanced to establish a path to the stenosis. Since the guide wire is separate from the catheter, torque applied to the guide wire to steer the guide wire through the vascular system and across the stenosis is not conveyed to any part of the catheter. Once a distal end of the guide wire is across the stenosis, the separate over-the-wire catheter is advanced over the guide wire until the balloon is positioned across the lesion.

One type of non-over-the-wire catheter has its own built in guide wire (sometimes referred to as a core wire) such that the core wire, balloon and inflation lumen comprise a single unit. Due to this single unit construction, torque (i.e., a rotational force) applied to a proximal end of a hypotube of the non-over-the-wire catheter (to which the core wire is fixedly attached) to steer the catheter through the vascular system and across the stenosis, is conveyed to other parts of the catheter.

In particular, torque induced rotation applied to the hypotube and core wire combination is transmitted to a distal end of the balloon and to a proximal end of a waist tube that extends about the core wire and couples the hypotube to the balloon. However, due to the tortuosity of portions of the guide catheter and of the patient's vascular system, the balloon and the waist tube may contact parts of the walls of the guide catheter guide lumen and the arterial vessels. This contact may cause rotation of portions of the balloon and the waist tube to lag behind rotation of the hypotube and core wire combination. The lag in balloon rotation dampens steering responsiveness of the balloon catheter itself, since contact of the balloon with the walls of the guide lumen and arterial vessels imparts drag to the distal end of the core wire. This, in turn, dampens the responsiveness of the core wire distal spring tip.

Typically, a spring tip is provided at the distal end of the core wire and is formed with a J-bend. The J-bend permits the balloon catheter to be steered into desired arterial branches. That is, torque induced rotation applied to the hypotube is transmitted to the spring tip through the core wire to position the J-bend to enter the desired arterial branch. A non-uniform ability to accurately position the J-bend of the spring tip, such as may be caused by a lag in balloon rotation which dampens steering responsiveness, makes the balloon catheter difficult to steer and may unnecessarily prolong the angioplasty procedure.

In addition, the lag in balloon rotation causes the balloon and the waist tube to twist upon themselves. The balloon tends to twist upon itself proximally from its distal attachment to the core wire, while the waist tube twists upon itself distally from its proximal attachment to the hypotube. If balloon twist is minimal, as a result of minimal steering torque applied to the hypotube, the balloon will untwist upon application of inflation fluid pressure to inflate the balloon once the balloon is positioned across a stenosis. However, if balloon twist is significant, the balloon may not inflate uniformly. Non-uniform balloon inflation exhibits balloon behavior wherein portions of the balloon (i.e., constrictions in the balloon due to twist) do not inflate to their maximum diameter. These under-inflated constrictions do not uniformly press the stenosis into the arterial wall and hence, do not effectively dilate the lesion to allow acceptable blood flow through the arterial vessel. In addition, upon deflation of the balloon, those segments of the balloon (i.e., segments adjacent the constrictions) which were fully inflated may not completely deflate. These partially deflated segments may make withdrawal of the balloon catheter from the patient's vascular system back through the guide catheter difficult.

It is desirable in a non-over-the-wire catheter to reduce the transmission of torque (applied to the hypotube and core wire combination) to the balloon of the catheter. The reduction in torque transmission would abate twisting of the balloon as the catheter is steered through the vascular system, and thereby permit uniform inflation and deflation of the balloon which is needed to effectively dilate the stenosis to re-establish an acceptable blood flow through the arterial vessel. In addition, the reduction in torque transmission, from the core wire to the balloon, would reduce, if not eliminate, the twisting of the balloon from the lag in balloon rotation upon the application of torque to the core wire. This reduction in balloon twist would alleviate steering difficulties sometimes associated with non-over-the-wire catheters wherein torque is readily transmitted from the core wire to the balloon.

SUMMARY OF THE INVENTION

The present invention is a catheter for use in angioplasty. The catheter includes an elongate flexible tubular member having an interior passage extending from a proximal end to a distal end. A guiding member having proximal and distal ends is secured at its proximal end to the tubular member adjacent its distal end, so that the guiding member extends distally beyond the distal end of the tubular member. An elongate flexible waist tube having proximal and distal ends is sealably connected at its proximal end to the tubular member adjacent its distal end, such that the waist tube extends distally beyond the distal end of the tubular member about the guiding member to define a distal interior passage in fluid communication with the interior passage of the tubular member. An inflatable balloon member extends around a section of the guiding member and has an interior in fluid communication with the distal interior passage of the waist tube. The balloon member includes a proximal end sealably connected to the distal end of the waist tube and a distal end that extends coaxially about a portion of the guiding member. An axially stiff component is coupled to the balloon member. The axially stiff component permits rotational movement of the guiding member relative to the balloon member, such that torque applied to guiding member through the tubular member is not readily transmitted to the balloon member. A push element associated with the guiding member is cooperable with the axially stiff component. The push element prevents a proximal longitudinal collapse of the balloon member and waist tube when the catheter is advanced through a patient's vascular system.

In one embodiment, the axially stiff component is an inner sleeve having a proximal end, a distal end and a through lumen. The through lumen extends between the proximal and distal ends of the inner sleeve and is adapted to freely receive the guiding member therethrough, such that the guiding member can rotate relative to the inner sleeve upon application of torque to the tubular member. The distal end of the inner sleeve is secured to the distal end of the balloon member, such that the inner sleeve extends proximally, coaxially along the guiding member. The inner sleeve exhibits a substantial degree of column strength to resist buckling when the catheter is advanced through a patient's vascular system. In this embodiment, the push element is a thrust ring secured to the guiding member. The thrust ring abuts the proximal end of the inner sleeve to prevent longitudinal displacement of the inner sleeve proximally along the guiding member. This, in turn, prevents the longitudinal collapse of the balloon member and waist tube in the proximal direction when the catheter is advanced through a patient's vascular system.

In further embodiments, the push element is integrally formed with the guiding member or takes the form of a thrust sphere. The inner sleeve may comprise various lengths of tubular stock or may be formed by a built up layer of adhesive material applied to an inner circumferential surface of the distal end of the balloon member. A cylindrical gap defined between an interior wall of the inner tube and the exterior surface of the guiding member may or may not be filled with a lubricating fluid. The cylindrical gap with or without the lubricating fluid provides resistance to pressurized balloon fluid flow to minimize leakage through the inner sleeve and distal end of the balloon member.

The non-over-the-wire catheter of the present invention is relatively uncomplicated and since the distal end of the balloon member is not coupled to the guiding member, the guiding member can be rotated relative to the balloon member with minimal twisting of the balloon member as the catheter is steered through the vascular system of a patient. This reduction in balloon twist permits uniform inflation and deflation of the balloon which is needed to effectively dilate the stenosis and re-establish acceptable blood flow through the arterial vessel.

Moreover, the non-transmission of torque from the guiding member to the balloon member reduces, if not eliminates balloon rotation. Hence, the effects (i.e, dampened steering responsiveness) due to the lag in balloon rotation upon application of torque to the guiding member are substantially decreased. The effects of balloon rotation lag are decreased and steering responsiveness improved, because contact between the balloon and the interior wall of a guide catheter and the walls of arterial vessels no longer imparts drag to the distal end of the guiding member. This lack of drag alleviates steering difficulties sometimes associated with non-over-the-wire catheters wherein torque is readily transmitted from the guiding member to the balloon.

In addition, the push element and the inherent column strength of the inner sleeve prevent the balloon member and waist tube from longitudinally collapsing along the guiding member as the catheter is being maneuvered through a vascular system of a patient.

BRIEF DESCRIPTION OF THE DRAWINGS

FIG. 1 is an elevational view of a first preferred embodiment of a balloon catheter in accordance with the present invention.

FIG. 2 is an enlarged sectional view of a distal end of the balloon catheter shown in FIG. 1.

FIG. 3 is a greatly enlarged sectional view similar to FIG. 2 showing details of the distal end of the first preferred embodiment of the balloon catheter.

FIG. 4 is a greatly enlarged cross sectional view taken along line 4—4 of FIG. 3.

FIG. 5 is a greatly enlarged sectional view showing details of a second embodiment of a distal end of a balloon catheter in accordance with the present invention.

FIG. 6 is a greatly enlarged sectional view showing details of a third embodiment of a distal end of a balloon catheter in accordance with the present invention.

FIG. 7 is a greatly enlarged sectional view showing details of a fourth embodiment of a distal end of a balloon catheter in accordance with the present invention.

FIG. 8 is a greatly enlarged sectional view showing details of a fifth embodiment of a distal end of a balloon catheter in accordance with the present invention.

FIG. 9 is a greatly enlarged sectional view showing details of a sixth embodiment of a distal end of a balloon catheter in accordance with the present invention.

FIG. 10 is a greatly enlarged cross sectional view taken along line 10—10 of FIG. 9.

DETAILED DESCRIPTION OF THE PREFERRED EMBODIMENTS

Figure 11:
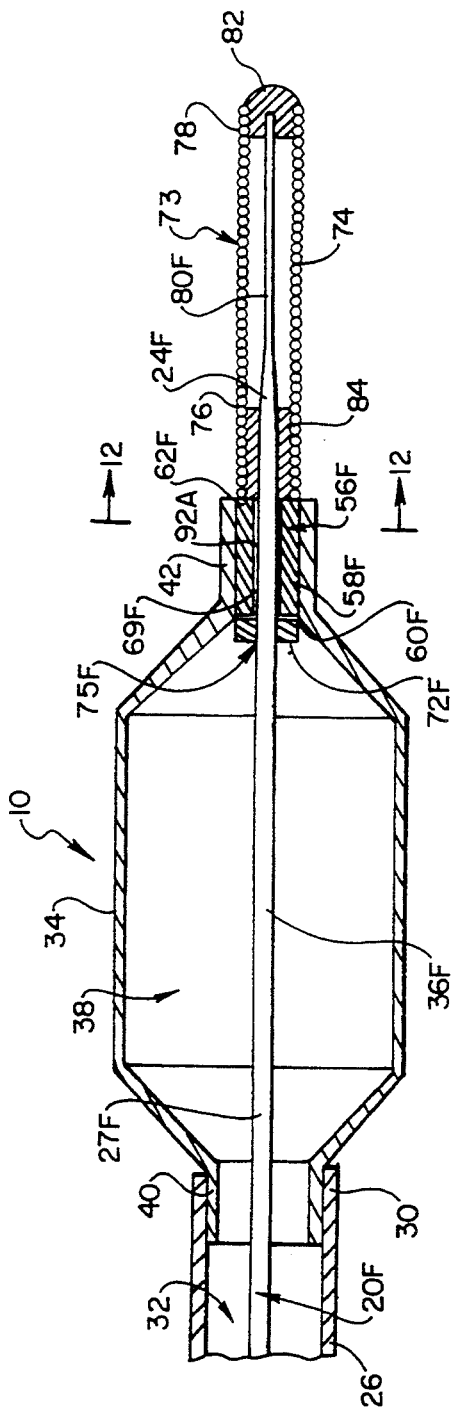
FIG. 11 is a greatly enlarged sectional view showing details of a seventh embodiment of a distal end of a balloon catheter in accordance with the present invention.

A non-over-the-wire catheter 10 in accordance with the present invention is illustrated generally in FIG. 1. The catheter 10 includes an elongate flexible tubular member 12 (i.e., hypotube) having an interior passage 14 (See FIG. 2) extending from a proximal end 16 to a distal end 18. As seen best in FIG. 2, a core wire 20 has a proximal end 22 and a distal end 24. The proximal end 22 of the core wire 20 is joined to the tubular member 12 adjacent to its distal end 18, with the core wire 20 extending distally beyond the distal end 18 of the tubular member 12.

The core wire 20 preferably provides varying flexibility along its length such that its flexibility increases in the distal direction. As illustrated in FIG. 2 (not shown to scale), this may be accomplished by having a core wire with one or more ground tapers. In one embodiment, the tubular member 12 is preferably formed from Type 304 stainless steel hypodermic tubing, and the core wire 20 is preferably formed from Type 304 stainless steel and manufactured by centerless grinding. The core wire 20 preferably has four main sections 21, 23, 25 and 27 and three tapered sections 29, 31 and 33. The core wire 20 is preferably stress relieved by exposing the wires before grinding to a temperature in a range of from 500° F. to 800° F. for a time period from about 30 min. to about 6 hours, and preferably at 750° F. for about 5 hours including ramp-up time. Preferably, the first section 21 is approximately 1.25 in. long and has a diameter of approximately 0.012 in. The second section 23 is approximately 4 in. long and has a diameter of approximately 0.0095 in. The third section 25 is approximately 3 in. long and has a diameter of approximately 0.0075 in. The fourth section 27 is approximately 2.5 in. long and has a diameter of approximately 0.0053 in. The first, second and third tapered sections 29, 31 and 33, respectively, are each approximately 1 in. in length.

The core wire 20 is preferably joined to the tubular member 12 by a braze material composed of a silver brazing metal powder with a brazing flux such as (BAg-7-325 mesh) available from Turbo-Braze, Corp. (Union, N.J.). Alternatively, the core wire 20 can be joined to the tubular member 12 by a silver solder material composed of 4% silver and 96% tin.

Other materials, such as a super elastic alloy (otherwise known as a shape memory alloy) may be used for the tubular member 12. For example, TINEL available from Raychem, Corp. (Menlo Park, Calif.) or a Nickel-Titanium shape memory alloy available from Shape Memory Applications, Inc. (Sunnyvale, Calif.). An adhesive material, such as cyanoacrylate, may be used to join a core wire 20 to a tubular member 12 composed of a super elastic alloy.

The catheter 10 further includes an elongate flexible waist tube 26 having a proximal end 28 and a distal end 30. The proximal end 28 of the waist tube 26 is sealably connected to the tubular member 12 adjacent its distal end 18. As seen best in FIG. 2, the waist tube 26 extends distally beyond the distal end 18 of the tubular member 12 and about the core wire 20 to define a distal interior passage 32. The distal interior passage 32 is in fluid communication with the interior passage 14 of the tubular member 12.

As seen in FIG. 2, an inflatable balloon member 34 extends about a section 36 of the core wire 20. The balloon member 34 has an interior 38 in fluid communication with the distal interior passage 32 of the waist tube 26. The balloon member 34 further includes a proximal end 40 and a distal end 42. The proximal end 40 of the balloon member 34 is sealably connected to the distal end 30 of the waist tube 26. The distal end 42 of the balloon member 34 extends coaxially about the core wire 20.

In one embodiment, the waist tube 26 is preferably formed of a polymer material, such as polyethelene. For example, PETROTHENE (HD, LB5003, HDPE) available from Quantum, USI Division (Cincinnati, Ohio). The balloon member 34 is preferably formed of a polymer material such as polyolefin which has been treated by radiation cross linking. The balloon member 34 may also be silicone coated. A suitable polyolefin is available from E. I. DuPont Nemours & Co. (Wilmington, Del.) under the tradename SURYLYN® (8527 POC) Ionomer. The waist tube 26 is preferably bonded to the tubular member 12 and to the balloon member 34 by a suitable adhesive and sealing material. For example, LOCTITE PRISM 405, a cyanoacrylate, available from Loctite, Corp. (Newington, Conn.) or TRA-BOND 2135D, an epoxy, available from Tra-Con, Inc. (Medford, Mass.).

As seen in FIG. 1, a manifold fitting 44 is mounted on the proximal end 16 of the tubular member 12 to facilitate connection with an inflation device (not shown) for the introduction and removal of pressurized balloon fluid to the catheter 10 to inflate and deflate the balloon member 34 via interior passage 14 and distal interior passage 32. The manifold fitting 44 includes a luer fitting 46 (for connection to the inflation device), a first end cap 48, a manifold body 50, a second end cap 52 and a strain relief tube 54.

In the preferred embodiment shown in FIGS. 2 and 3, the catheter 10 further includes an axially stiff component 56 defined by a inner sleeve 58 having a proximal end 60 and a distal end 62. A through lumen 64 extends between the proximal end 60 and the distal end 62 of the inner sleeve 58. The distal end 62 of the inner sleeve 58 is sealed and secured to an inner circumferential surface 66 of the distal end 42 of the balloon member 34 by a suitable adhesive and sealing material 67 (see FIG. 4). For example, LOCTITE PRISM 405, a cyanoacrylate, available from Loctite, Corp. (Newington, Conn.) or TRA-BOND 2135D, an epoxy, available from Tra-Con, Inc. (Medford, Mass.).

The through lumen 64 of the inner sleeve 58 is configured to freely receive the core wire 20, such that the core wire 20 can freely rotate relative to the inner sleeve 58 upon the application of torque to the proximal end 16 of the tubular member 12. The inner sleeve 58 extends proximally, coaxially along the core wire 20 from the distal end 42 of the balloon member 34. The through lumen 64 defines a cylindrical gap 68 between an interior wall 69 of the inner sleeve 58 and an exterior surface 71 of the core wire 20 (see FIG. 4). The cylindrical gap 68 has a minimal radial dimension (on the order of 0.0001"–0.0003") to provide resistance to flow of pressurized balloon fluid, to minimize leakage through the inner sleeve 58 and the distal end 42 of the balloon member 34.

In the preferred embodiment shown in FIGS. 2 and 3, the catheter 10 further includes a push element defined by a thrust ring 72 secured to the core wire 20 in the area of the proximal end 40 of the balloon member 34. The thrust ring 72 has a central aperture 75 adapted to receive the core wire 20. The thrust ring 72 abuts the proximal end 60 of the inner sleeve 58 so as to prevent a longitudinal displacement of the inner sleeve 58 proximally along the core wire 20. This, in turn, prevents the longitudinal collapse of the balloon member 34 and the waist tube 26 in a proximal direction when the catheter 10 is advanced through a patient's vascular system. The thrust ring 72 rotates with the core wire 20 and relative to the inner sleeve 58 upon the application of torque to the proximal end 16 of the tubular member 12.

The inner sleeve 58 that defines the axially stiff component 56 is preferably tubular stock formed from a polyimide, such as is available from HV Technologies, Inc. (Trenton, Ga.). Alternatively, the inner sleeve 58 may be formed from a polyethylene terephthalate (PET). The inner sleeve 58 exhibits a substantial degree of column strength to resist axial buckling when the catheter 10 is advanced through a patient's vascular system.

The thrust ring 72 is preferably formed from a platinum alloy composed of 90% Pt and 10% Ir such as is available from Uniform Tubes, Inc. (Collegeville, Pa.). Alternatively, the thrust ring 72 may be tubular stock formed from a polyimide, such as is available from HV Technologies, Inc. (Trenton, Ga.) or the thrust ring 72 may be formed from Type 304 stainless steel. The thrust ring 72 is preferably radiopaque to facilitate fluoroscopy viewing of the catheter 10. The thrust ring 72 (formed preferably of platinum alloy or alternatively of stainless steel) is preferably secured to the core wire 20 by a braze material composed of a silver brazing metal powder with a brazing flux such as (BAg-7-325 mesh) available from Turbo-Braze, Corp. (Union, N.J.). Alternatively, this thrust ring 72 can be secured to the core wire 20 by a silver solder material composed of 4% silver and 96% tin. A thrust ring 72 alternatively formed of a polyimide may be secured to the core wire 20 by a suitable adhesive substance. For example, LOCTITE PRISM 405, a cyanoacrylate, available from Loctite, Corp. (Newington, Conn.), or TRA-BOND 2135D, an epoxy, available from Tra-Con, Inc. (Medford, Mass.).

The inner sleeve 58 and thrust ring 72 combination permits rotation of the core wire 20 relative to the balloon member 34, upon the application of torque to the proximal end 16 of the tubular member 12 (such as may be applied to steer the catheter 10 through the vascular system of a patient to position the balloon member 34 across a stenosis). This torque, conveyed along the core wire 20, is not readily transmitted to the balloon member 34 from the core wire 20. Therefore, torque from the core wire 20 results in minimal, if any, twisting of the balloon member 34 and the waist tube 26. This translates into increased steering responsiveness of the catheter 10, since balloon rotation is virtually eliminated, along with the effects of balloon rotation lag.

As seen in FIG. 3, the catheter 10 further includes a radiopaque spring tip 73 positioned distally of the distal end 62 of the tubular element 58. The spring tip 73 includes a flexible, helical coil member 74 having a proximal end 76 and a distal end 78. The helical coil member 74 is preferably formed from radiopaque platinum alloy wire composed of 90% Pt and 10% Ir. The spring tip 73 is preferably 25 mm in length with varying flexibility. Alternatively, the spring tip 73 may be 15 mm in length with varying flexibility. A shaping ribbon 80 is integral with the core wire 20. A first joint 82, preferably comprising a weld, connects the distal end 78 of the coil member 74 to the shaping ribbon 80. A second joint 84 couples the proximal end 76 of the coil member 74 to the distal end 24 of the core wire 20. The second joint 84 preferably comprises a solder joint consisting of a silver solder material composed of 4% silver and 96% tin. Alternatively, the second joint 84 may comprise a braze joint consisting of a braze material composed of a silver brazing metal powder with a brazing flux such as (BAg-7-325 mesh) available from Turbo-Braze, Corp. (Union, N.J.).

In a second embodiment of the catheter 10 illustrated in FIG. 5, the thrust ring 72A is secured to the modified core wire 20A in the area of the waist tube 26 located proximally of the proximal end 40 of the balloon member 34. The inner sleeve 58A (which is longer than the inner sleeve 58 of the first preferred embodiment) extends from the distal end 42 of the balloon member 34 proximally to the thrust ring 72A. Due to its longer length, the inner sleeve 58A has less column strength. However, the longer length of the inner sleeve 58A adds column strength to the core wire 20A and thereby increases the pushability of the catheter 10. In addition the longer length of the inner sleeve 58A decreases the flexibility of the catheter 10 at its distal end.

In a third embodiment of the catheter 10 illustrated in FIG. 6, the thrust ring 72B is secured to the core wire 20B immediately adjacent and proximal to the distal end 42 of the balloon member 34. The inner sleeve 58B (which is shorter than the inner sleeve 58 of the first preferred embodiment) is positioned entirely within the distal end 42 of the balloon member 34. Due to its shorter length, the inner sleeve 58B has greater column strength. However, the shorter length of the inner sleeve 58B adds minimal column strength to the core wire 20B. In addition, the shorter length of the inner sleeve 58A increases the flexibility of the catheter 10 at its distal end.

In a fourth embodiment of the catheter 10 illustrated in FIG. 7, the push element is defined by a thrust sphere 72C secured to the modified core wire 20C in a position similar to that shown in relation to the second embodiment of FIG. 5. The thrust sphere 72C has a central aperture 75C adapted to receive the core wire 20C. The inner sleeve 58C is identical to the inner sleeve 58A of the second embodiment of FIG. 5.

In a fifth embodiment of the catheter 10 illustrated in FIG. 8, the push element is integrally formed with the modified core wire 20D. The core wire 20D includes a distal portion 86, an enlarged portion 88 and a transition portion defined by a tapered thrust ledge 90. The thrust ledge 90 defines the push element. The thrust ledge 90 is positioned similar to the thrust ring 72A of the second embodiment (see FIG. 5). The inner sleeve 58D is identical to the inner sleeve 58A of the second embodiment of FIG. 5.

In a sixth embodiment of the catheter 10 illustrated in FIGS. 9 and 10, the inner sleeve 58E has a larger through lumen 64E than that shown in regards to the first preferred embodiment of FIGS. 2 and 3. Hence, the radial dimension of the cylindrical gap 68E between the interior wall 69E of the inner sleeve 58E and an exterior surface 71 of the core wire 20 is increased. In this embodiment the cylindrical gap 68E is filled with a lubricating fluid 92 that provides resistance to flow of pressurized balloon fluid, to minimize leakage through the inner sleeve 58E and the distal end 42 of the balloon member 34. The lubricating fluid 92 is preferably TEFLON. Alternatively, the lubricating fluid 92 may be a hydrogel polyethylene oxide (PEO), silicone or graphite. The positioning of the thrust ring 72E and the length of the inner sleeve 58E is similar to that shown in regards to the first preferred embodiment (see FIGS. 2 and 3).

Figure 12:
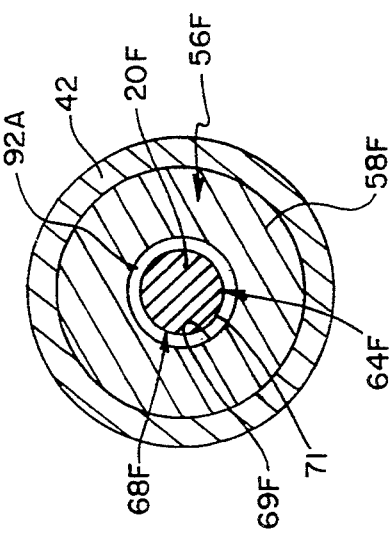
FIG. 12 is a greatly enlarged cross sectional view taken along line 12—12 of FIG. 11.

In a seventh embodiment of the catheter 10 illustrated in FIGS. 11 and 12, the inner sleeve 58F is a built up layer of adhesive material applied to the inner circumferential surface 66 of the distal end 42 of the balloon member 34. The built up adhesive material that defines the inner sleeve 58F is preferably an epoxy, such as TRA-BOND 2135D, available from Tra-Con, Inc. (Medford, Mass.). Alternatively, the built up adhesive material that defines the inner sleeve 58F is a urethane with solvent or a cyanoacrylate. In this embodiment the cylindrical gap 68F is filled with a lubricating fluid 92A that provides resistance to flow of pressurized balloon fluid, to minimize leakage through the inner sleeve 58F and the distal end 42 of the balloon member 34. The lubricating fluid 92A is preferably TEFLON. Alternatively, the lubricating fluid 92A may be a hydrogel polyethylene oxide (PEO), silicone or graphite. The positioning of the thrust ring 72F and the length of the inner sleeve 58F is similar to that shown in regards to the third embodiment (see FIG. 6).

The non-over-the-wire catheter 10 of the present invention is relatively uncomplicated and since the distal end 42 of the balloon member 34 is not coupled to the core wire 20, the core wire 20 can be rotated relative to the balloon member 34 with minimal twisting of the balloon member 34 as the catheter 10 is steered through the vascular system of a patient. This reduction in balloon twist permits uniform inflation and deflation of the balloon member 34 which is needed to effectively dilate the stenosis and re-establish acceptable blood flow through the arterial vessel.

Moreover, the non-transmission of torque from the core wire 20 to the balloon member 34 reduces, if not eliminates balloon rotation. Hence, the effects (i.e., dampened steering responsiveness) due to the lag in balloon rotation upon application of torque to the core wire 20 are substantially decreased. The effects of balloon rotation lag are decreased and steering responsiveness improved, because contact between the balloon member 34 and the inner wall of a guide catheter and the walls of arterial vessels no longer imparts drag to the distal end 24 of the core wire 20. This lack of drag alleviates steering difficulties sometimes associated with non-over-the-wire catheters wherein torque is readily transmitted from the core wire to the balloon. In addition, the push element and the inherent column strength of the inner sleeve prevent the balloon member 34 and waist tube 26 from longitudinally collapsing along the core wire 20 as the catheter 10 is being maneuvered through a vascular system of a patient.

Although the present invention has been described with reference to preferred embodiments, workers skilled in the art will recognize that changes may be made in form and detail without departing from the spirit and scope of the invention. For example, in considering a preferred commercial embodiment of the catheter of the present invention, it is contemplated that the distal end of the catheter would include a strain relief assembly as disclosed in the commonly assigned application entitled Dilatation Catheter Strain Relief Assembly (Ser. No. 07/852,548) which was filed on even date with this application and which is hereby incorporated herein in its entirety by reference thereto.

What is claimed is:

1. A catheter adapted to be inserted into a patient's vascular system, the catheter comprising:

an elongate flexible tubular member having an interior passage extending from a proximal end to a distal end;

a guiding member having a proximal end and a distal end, the proximal end of the guiding member being coupled to and fixed against rotational movement relative to the tubular member, the guiding member extending distally beyond the distal end of the tubular member;

a flexible waist tube having a proximal end and a distal end, the waist tube being more flexible than the tubular member, the waist tube having its proximal end sealably connected to the tubular member, the waist tube extending distally beyond the distal end of the tubular member about the guiding member to define a distal interior passage in fluid communication with the interior passage of the tubular member;

an inflatable balloon member extending around a section of the guiding member and having an interior in fluid communication with the interior passages, the balloon member including a proximal end sealably connected to the distal end of the waist tube and a distal end free from any fixed connection to the guiding member;

an axially stiff component coupled to the balloon member so as to allow rotational movement of the guiding member relative to the balloon member such that torque applied through the guiding member is not readily transmitted to the balloon member from the guiding member, the axially stiff component is an inner sleeve having a proximal end, a distal end, and a through lumen that extends between the proximal and distal ends of the inner sleeve, the inner sleeve exhibiting a substantial degree of column strength to resist axial buckling when the catheter is advanced through a patient's vascular system, and the distal end of the inner sleeve is secured to the distal end of the balloon member, and the through lumen of the inner sleeve is dimensioned to freely receive the guiding member and to define a cylindrical gap between an interior wall of the inner sleeve and an exterior surface of the guiding member, the cylindrical gap having minimum radial dimension to provide resistance to flow of pressurized balloon fluid, to minimize leakage through the inner sleeve and distal end of the balloon member; and push means associated with the guiding member and cooperable with the axially stiff component for preventing a longitudinal collapse of the balloon member in a proximal direction when the catheter is advanced through a patient's vascular system.

2. The catheter of claim 1 wherein the distal end of the inner sleeve is secured to the distal end of the balloon member, such that the inner sleeve extends proximally along the catheter from the distal end of the balloon member.

3. The catheter of claim 1 wherein the through lumen of the inner sleeve is dimensioned to freely receive the guiding member, such that the guiding member can rotate relative to the inner sleeve upon the application of torque through the guiding member.

4. The catheter of claim 2 wherein the distal end of the inner sleeve is secured to the distal end of the balloon member, such that the inner sleeve extends proximally, coaxially along the guiding member from the distal end of the balloon member.

5. The catheter of claim 4 wherein the push means is a push element secured to the guiding member, the push element abutting the proximal end of the inner sleeve so as to prevent a longitudinal displacement of the inner sleeve proximally along the guiding member, and thereby prevent the longitudinal collapse of the balloon member and waist tube in the proximal direction when the catheter is advanced through a patient's vascular system.

6. The catheter of claim 5 wherein the push element is a thrust ring having a central aperture adapted to receive the guiding member, the thrust ring rotating with the guiding member and relative to the inner sleeve upon the application of torque through the guiding member.

7. The catheter of claim 5 wherein the push element is a thrust sphere having a central aperture adapted to receive the guiding member, the thrust sphere rotating with the guiding member and relative to the inner sleeve upon the application of torque through the guiding member.

8. The catheter of claim 5 wherein the push element is secured to the guiding member by an adhesive material.

9. The catheter of claim 5 wherein the push element is secured to the guiding member by solder.

10. The catheter of claim 5 wherein the push element is secured to the guiding member by braze.

11. The catheter of claim 4 wherein the push means is a push element integrally formed with the guiding member, the push element abutting the proximal end of the inner sleeve so as to prevent a longitudinal displacement of the inner sleeve proximally along the guiding member, and thereby prevent the longitudinal collapse of the balloon member and waist tube in the proximal direction when the catheter is advanced through a patient's vascular system.

12. The catheter of claim 5 wherein the guiding member includes a distal portion, an enlarged proximal portion and a transition portion between the proximal and distal portions that defines the push element.

13. The catheter of claim 12 wherein the transition portion is a tapered thrust ledge that allows the guiding member to rotate relative to the inner sleeve upon the application of torque through the guiding member.

14. The catheter of claim 4 wherein the distal end of the balloon member has an inner circumferential surface to which the distal end of the inner sleeve is secured.

15. The catheter of claim 14 wherein the distal end of the inner sleeve is secured to the balloon member by an adhesive material.

16. The catheter of claim 15 wherein the adhesive material is epoxy.

17. The catheter of claim 15 wherein the adhesive material is cyanoacrylate.

18. The catheter of claim 1, and further including:
a flexible, helical coil member having a proximal end and a distal end, the coil member being mounted on the distal end of the guiding member distally of the distal end of the balloon member.

19. The catheter of claim 18, and further including:
a shaping ribbon extending between and connecting the distal end of the coil member to the distal end of the guiding member.

20. The catheter of claim 19 wherein a first fused joint connects the distal end of the coil member to the shaping ribbon, and wherein a second fused joint couples the proximal end of the coil member to the distal end of the guiding member.

21. A catheter adapted to be inserted into a patient's vascular system, the catheter comprising:
a proximal tube having a through passage extending from a proximal end to a distal end;
a guiding member having a proximal end and a distal end, the proximal end of the guiding member being coupled to and fixed against rotational movement relative to the proximal tube, the guiding member extending distally beyond the distal end of the proximal tube;
a flexible waist tube having a proximal end and a distal, the waist tube being more flexible than the proximal tube, the waist tube having its proximal end sealably connected to the proximal tube, the waist tube extending distally beyond the distal end of the proximal tube about the guiding member to define a distal interior passage in fluid communication with the through passage of the proximal tube;
an inflatable balloon member extending around a section of the guiding member and having an interior in fluid communication with the interior passage of the waist tube, the balloon member including a proximal end sealably connected to the distal end of the waist tube and a distal end free from any fixed connection to the guiding member;
an inner sleeve having a proximal end, a distal end and through lumen extending between the proximal and distal ends of the inner sleeve, the inner sleeve exhibiting a substantial degree of column strength to resist axial buckling when advancing the catheter through a patient's vascular system, the distal end of the inner sleeve being secured to the distal end of the balloon member and the through lumen of the inner sleeve being dimension to freely receive the guiding member and defining a cylindrical gap between an interior wall of the inner and an exterior surface of the guiding member, the cylindrical gap being filled with a lubricating fluid providing resistance to flow of pressurized balloon fluid, minimizing leakage through the inner sleeve and distal end of the balloon member; and
push means associated with the guiding member and cooperable with the inner sleeve for preventing a longitudinal collapse of the balloon member in the proximal direction when the catheter is advances through a patient's vascular system.

22. A catheter adapted to be inserted into a patient's vascular system, the catheter comprising:
a proximal tube having a through passage extending from a proximal end to a distal end;
a guiding member having a proximal end and a distal end, the proximal end of the guiding member being coupled to and fixed against rotational movement relative to the proximal tube, the guiding member extending distally beyond the distal end of the proximal tube;
a flexible waist tube having a proximal end and a distal end, the waist tube being more flexible than the proximal tube, the waist tube having its proximal end sealably connected to the proximal tube, the waist tube extending distally beyond the distal end of the proximal tube about the guiding member to define a distal interior passage in fluid communication with the interior passage of the proximal tube;

an inflatable balloon member extending around a section of the guiding member and having an interior in fluid communication with the interior passage of the waist tube, the balloon member including a proximal end sealably connected to the distal end of the waist tube and a distal end free from any fixed connection to the guiding member;

an inner sleeve having a proximal end, a distal end and through lumen extending between the proximal and distal ends of the inner sleeve, the inner sleeve exhibiting a substantial degree of column strength to resist axial buckling when advancing the catheter through a patient's vascular system, the through lumen of the inner sleeve being dimensioned to freely receive the guiding member, such that the guiding member can rotate relative to the inner sleeve upon the application of torque through the guiding member, the inner sleeve including a built-up layer of adhesive material applied to an inner circumferential surface of the distal end of the balloon member; and push means associated with the guiding member in cooperable relation with the inner sleeve for preventing longitudinal collapse of the balloon member in a proximal direction when the catheter is advanced through a patient's vascular system.

* * * * *